US008565871B2

(12) United States Patent
Tuysserkani

(10) Patent No.: US 8,565,871 B2
(45) Date of Patent: Oct. 22, 2013

(54) AUTOMATED EXTERNAL DEFIBRILLATOR DEVICE WITH INTEGRATED WIRELESS MODEM

(75) Inventor: Bijan B. Tuysserkani, Boulder, CO (US)

(73) Assignee: QUALCOMM Incorporated, San Diego, CA (US)

( * ) Notice: Subject to any disclaimer, the term of this patent is extended or adjusted under 35 U.S.C. 154(b) by 876 days.

(21) Appl. No.: 12/554,975

(22) Filed: Sep. 7, 2009

(65) Prior Publication Data
US 2011/0060378 A1    Mar. 10, 2011

(51) Int. Cl.
*A61N 1/39*  (2006.01)
*G08B 1/08*  (2006.01)
*A61B 5/00*  (2006.01)

(52) U.S. Cl.
CPC ............. *A61N 1/39* (2013.01); *A61B 5/0022* (2013.01)
USPC ............................ 607/5; 607/60; 340/539.12

(58) Field of Classification Search
USPC .................. 607/5, 60; 340/539.12, 539.13
See application file for complete search history.

(56) References Cited

U.S. PATENT DOCUMENTS

| 6,738,671 | B2 * | 5/2004 | Christophersom et al. ..... 607/60 |
| 6,747,556 | B2 * | 6/2004 | Medema et al. ......... 340/539.12 |
| 2002/0103508 | A1 * | 8/2002 | Mathur ............................. 607/5 |
| 2003/0212311 | A1 * | 11/2003 | Nova et al. .................... 600/300 |
| 2003/0233129 | A1 * | 12/2003 | Matos ................................ 607/5 |
| 2004/0172069 | A1 * | 9/2004 | Hakala .............................. 607/5 |
| 2005/0251213 | A1 * | 11/2005 | Freeman ........................... 607/5 |
| 2006/0069326 | A1 | 3/2006 | Heath |
| 2006/0287586 | A1 * | 12/2006 | Murphy ........................ 600/300 |
| 2009/0005827 | A1 | 1/2009 | Weintraub et al. |

FOREIGN PATENT DOCUMENTS

| JP | 2006512156 A | 4/2006 |
| WO | 2004061746 A2 | 7/2004 |

OTHER PUBLICATIONS

International Search Report and Written Opinion—PCT/US2010/048009, International Search Authority—European Patent Office—Dec. 13, 2010.

* cited by examiner

*Primary Examiner* — Carl H Layno
*Assistant Examiner* — Jessica Sarcione
(74) *Attorney, Agent, or Firm* — James T. Hagler

(57) ABSTRACT

An automatic external defibrillator (AED) includes an integral wireless modem configured so that, upon activation, the AED automatically connects to a wireless network and reports the event to an emergency services center or remote server to call for an ambulance. The activation report may be accomplished by calling an emergency services center and playing a prerecorded voice message that includes AED location information. Alternatively, the activation report may be transmitted via a wireless data network to a remote server which routes the information to appropriate authorities. After the activation report is transmitted, the AED may transmit patient and treatment data to the server. The AED may include a speaker phone capability so a caregiver can talk with a dispatcher or medical team. The AED may also automatically report activation data and periodic self-diagnostic testing results to a manufacturer or service provider via a wireless data call to a remote server.

42 Claims, 12 Drawing Sheets

AUTOMATED EXTERNAL DEFIBRILLATOR DEVICE WITH INTEGRATED WIRELESS MODEM

FIELD OF THE INVENTION

The present invention relates generally to automatic external defibrillators (AEDs), and more particularly to an AED equipped with autonomous communication capabilities.

BACKGROUND

Automated External Defibrillators (AEDs) have improved survival of heart attack patients tremendously since their introduction. AEDs enable laypeople to diagnose and treat various life threatening arrhythmias, providing more life saving benefits than conventional traditional cardiopulmonary resuscitation (CPR) techniques. AEDs are now deployed in many public locations (e.g., schools, shopping malls, airports, etc.), as well as in workplaces. In 2006 the U.S. market alone for AEDs was estimated to be $300 million.

SUMMARY

Various embodiments provide an AED with an integrated wireless modem, such as a mobile station modem (MSM) chipset, coupled to an antenna. The embodiment devices and methods enable the AED to automatically place calls to a remote server or telephone number when the AED is activated, such as to report activation of the AED, summon emergency services and to relay patient vital signs and treatment data. In an embodiment, upon activation of the AED, the wireless modem can place a voice call to 911 emergency dispatch and relay important information, such as location and the nature of the emergency. In another embodiment, the AED may establish a wireless data connection to a remote server to transmit an activation announcement message, along with patient medical and treatment data so such patient data can be presented to paramedics or doctors. In another embodiment, the AED device may be equipped with a speaker and microphone, and be configured to place a voice call to emergency services so that an aid-giver can speak with dispatchers or medical personnel while attending to the patient. An embodiment may track the status of data and voice connections and assure that calls are re-established if they are accidentally dropped. In an embodiment, the AED may also be equipped with a global positioning system (GPS) capability so the activation report can include the precise location of the victim.

In a further embodiment, the AED may be configured to establish a data link and transmit usage, treatment, and patient vital signs information to a remote server after an AED treatment event is concluded. Such reporting of usage information may be transmitted to a medical facility (e.g., a nearby emergency room), a centralized emergency services database, and/or a database of the AED manufacturer.

In a further embodiment, the AED device may be configured to send results of periodic self-monitoring status checks to a remote server (e.g., a server of an AED servicing center or AED manufacturer), and to report servicing requirements along with AED location information.

BRIEF DESCRIPTION OF THE DRAWINGS

The accompanying drawings, which are incorporated herein and constitute part of this specification, illustrate aspects of the invention, and, together with the general description given above and the detailed description given below, serve to explain features of the invention.

DETAILED DESCRIPTION

Figure 1:
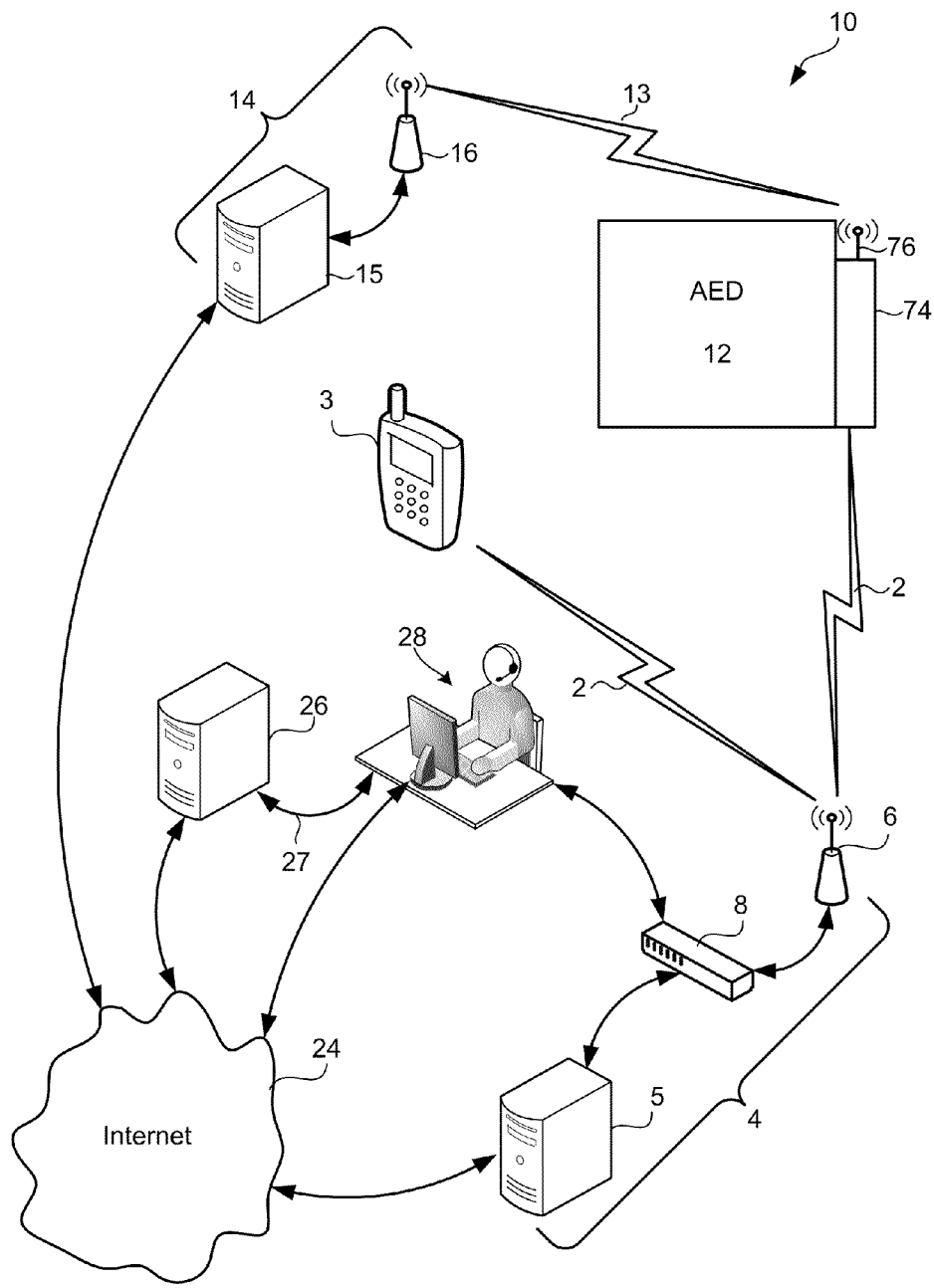
FIG. 1 is a system block diagram of a communication system useable with an embodiment.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

As used herein, the terms "automatic external defibrillator" and "AED" refer to any portable device designed to be used for cardiac resuscitation which includes a battery, charger, memory device, and electrodes or paddles for administering an electric shock to a patient.

As used herein, the term "server" refers to any of a variety of commercially available computer systems configured to operate in a client-server architecture. In particular, the term "server" refers to network servers, particularly Internet accessible servers, which typically include a processor, memory (e.g., hard disk memory), and network interface circuitry configured to connect the server processor to the network, such as the Internet, an instant messaging network, a simple messaging system network and/or a cellular telephone network.

The deployment of AEDs in public places has led to an overall decline in the number of deaths due to sudden cardiac events. Proper use of an AED can save the life of a person undergoing a cardiac event by stimulating the heart to begin beating when it has stopped, or by restoring a normal rhythm when the heart has begun to fibrillate.

Current CPR protocols advise placing a telephone call to an emergency services center (911, or the equivalent in other countries) to summon additional help from Advanced Life Support (ALS) services (e.g., an ambulance) as soon as possible. Typically, a bystander witnessing a cardiac event will use an AED device on the victim suffering the emergency, while another person calls emergency services and summons an ambulance. However, if there is only one person on the scene at the time, making this 911 call may delay CPR treatment with the AED. In a case where no second person is present to telephone emergency services, the current emergency training protocol advises the first responder finding a person who has collapsed to immediately call 911 to summon ALS assistance. After speaking to the emergency services dispatcher, the lone caller may attempt to resuscitate the victim by using the AED on the victim in combination with manual CPR techniques. If a bystander observes the person collapse, they are to provide CPR for two minutes before calling emergency services (e.g., 911).

Since the person placing the call to emergency services is rarely a medical professional, miscommunication may occur during the 911 call. The person who calls emergency services may not be able to provide clear or complete information that would enable the emergency dispatcher to accurately determine the location, nature, and severity of the medical emergency. Without such information, the dispatcher may not be able direct an emergency response team to the scene of the emergency or prepare them for what they will face. The person who calls 911 may also have little or no training in using an AED, and may benefit from guidance during its use. However, unless a second person is on the scene to remain on the telephone with the emergency dispatcher, it is very difficult for a rescuer to receive guidance from an emergency services telephone dispatcher while simultaneously operating an AED. Direct, simultaneous communication of data and voice communications through the AED device itself while it is in use would solve both these problems.

When a telephone call is placed to an emergency services center (e.g., by dialing 911), the caller is typically routed to an emergency services dispatcher at the appropriate local Public Safety Answering Point (PSAP). A PSAP is an emergency services center that answers telephone calls to 911 and dispatches the appropriate police, fire or medical emergency services personnel. The dispatcher asks the caller questions about the nature of the emergency, and verifies the location of the emergency and the telephone number of the caller. Most PSAPs use an Enhanced 911 communications system that will automatically obtain the telephone number of the caller, pull the associated address from a separate address database (usually maintained by the local telephone carrier), and automatically display the address and telephone number on the dispatcher's computer screen. Many PSAPs also have the ability to obtain location information from cellular telephones that are equipped with GPS receivers.

It is standard procedure for emergency dispatchers to verify the telephone and address information with callers for several reasons. First, the database from which the address information is automatically pulled by Enhanced 911 systems may contain errors. Second, although the address of the caller displays in many cases, the dispatcher may require additional information to pinpoint the exact location of the emergency within a building or at an address. For example, the emergency may have taken place in an office building containing many suites, at an athletic facility, or in the backyard of a residence. Finally, if the caller is using a handheld device, his or her telephone number may not automatically display on the dispatcher's computer screen. Not all Enhanced 911 systems have the capability to automatically obtain the telephone number and precise location of a caller who is using a wireless communication network.

The PSAP dispatcher typically types the collected information into various pre-set fields on a computer screen for entry into an incoming call database. Once the basic information is obtained, the dispatcher sends a dispatch request to an ALS team, while simultaneously transmitting the inputted basic data about the nature of the event to emergency rescuers via mobile data terminals located in emergency services vehicles.

No matter when a telephone call is placed to emergency services, the information conveyed may be incomplete. The person who first calls emergency services from the scene of a cardiac emergency is usually not a medical professional, and may be feeling a great deal of stress or panic. Therefore, he or she may not be able to accurately and completely convey information about the state of the victim to the telephone dispatcher at the emergency services call center. In addition, the emergency services telephone dispatcher may not be a trained medical professional, and thus may not be able to fully and properly interpret the details in the information from the caller. Regardless of whether data is correctly communicated, PSAP dispatchers are trained to input standardized factual information designed to give arriving ALS teams an overview of the situation. PSAP operators are trained to obtain basic facts about an emergency situation as quickly as possible, not to spend time on detailed medical diagnostic questions. Thus, ALS teams have little or no medical diagnostic information on the state of the victim before arriving at the scene of the emergency.

The caller may also miss details in verifying the exact location of the emergency. This may be due to stress, panic, or unfamiliarity with the location. Incorrect location information can be a fatal error, as it causes delays in the arrival of the ALS team.

If there is only one caregiver on the scene when a cardiac event occurs, a delay in reviving the victim may result while the sole caregiver calls emergency services and speaks to the dispatcher. In a cardiac emergency, a delay of even a few minutes in beginning resuscitation efforts may prove fatal to the victim. The sooner the victim is treated with CPR and/or an AED, the greater the chances of survival, and the less likely the victim will suffer irreversible damage to the heart. On the other hand, AED user instructions and training emphasize calling 911 (or other emergency number) before giving CPR and applying the AED, because early arrival of the ALS team is also critical to the patient's survival, and because CPR activities could delay the call for help by several minutes. Thus, the lone caregiver situation represents a difficult challenge for saving victims of sudden cardiac events using AEDs.

An AED records patient data and treatment data when is it is used, including recording ambient noises in some devices. Such recorded information may be useful to doctors for determining the patient's condition and the nature and timing of any resuscitation or defibrillation treatments applied before the arrival of medically trained personnel. However, such information must be downloaded and saved after the AED is deactivated. This information may be saved on a computer system of the responding ALS team (e.g., at a hospital, fire station, etc.). The information may later be collected and used by the AED manufacturer. Such information is not available to medical personnel while the AED is in use, and downloading the information from memory takes further time.

AEDs must also be serviced periodically to ensure that they remain in working order. Although an AED may have the ability to self-test for some functionalities, a service visit is required to recognize, diagnose and resolve any serious problem. Although regular service visits may be scheduled, if a problem occurs between service visits, a fault may not be detected and repaired until someone happens to notice that the AED is signaling that it is experiencing a problem.

The various embodiments resolve these current shortcomings in AEDs and the challenges faced by a lone caregiver by integrating a wireless modem, such as a mobile station modem (MSM) chipset, into the AED system and configuring the system to use the modem to communicate autonomously. In an embodiment, as soon as the AED is activated, the wireless modem is activated to place a call to 911 emergency dispatch or establish a data link to a remote server in order to provide its location information to a dispatcher. The AED's location information can be prerecorded or obtained from an internal Global Positioning System (GPS) receiver or via assisted GPS. In this manner, emergency services can be promptly informed of a cardiac emergency, including its accurate location (which may be different from the AED storage location). Once the call to emergency services has been completed or an AED activation message has been sent to a remote server, an embodiment AED can transmit patient diagnostic and treatment data to a remote server via a wireless data communication link. Transmitting such data to a remote server may allow the data to be routed via network protocols to medical and emergency response personnel so they can assess the patient's condition and be prepared to respond accordingly when they arrive on scene or when the patient arrives at a hospital emergency room.

In a further embodiment, the AED may be configured to enable a speaker phone voice call with a PSAP call center or telephone trauma center to provide communications between medical personnel and the caregivers via a speaker phone. This voice call may be activated by the AED autonomously, by the remote server, or in response to commands from medical personnel monitoring data transmissions. In a further embodiment, the AED may be configured with software to accept a voice-over-Internet (VoIP) call via an open IP connection so that medical personnel monitoring a patient's data may begin speaking to the caregiver (and patient, if the patient is conscious) without the need to establish a separate voice call. Since the AED of the various embodiments includes the circuitry and programming to automatically place the call to 911 or transmit an activation message to a remote server, transmit vital information to emergency dispatch, transmit patient data to medical and emergency personnel, and optionally establish a voice call via a speaker phone, a lone caregiver can immediately attend to the victim and begin CPR without delaying the arrival of trained medical personnel. Further, a lone caregiver can be coached by remote medical personnel without requiring the caregiver to hold a telephone or place a call. Moreover, the automatic activation reporting will reduce errors in reporting an emergency, enabling quicker responses by ALS teams.

Integrating a wireless modem within the AED also provides reliability benefits, since the AED can be configured to automatically report results of periodic self-diagnostic testing. When the AED is scheduled for a periodic self-diagnostic test, the wireless modem may be activated so that the results of the test can be reported to a remote server, such as the server of the AED manufacturer or service provider. Using this data, the AED manufacturer or service provider can anticipate when servicing will be required, such as to replace the battery. Further, if the AED self-diagnostic test reveals a fault condition, the AED manufacturer or service provider can be notified so that the device can be promptly replaced or repaired. This will reduce the likelihood that, in the event of an emergency, it is discovered that the AED is nonfunctional.

FIG. 1 shows a communication network 10 that may be used with the various embodiments. Such a communication network 10 includes one or more AEDs 12 that include a wireless modem 74 connected to an antenna 76 for transmitting and receiving cellular signals 2 from/to a base station 6 within a cellular telephone network 4. In this example communication network 10, the base station 6 is a part of a cellular network 4 that includes elements required to operate the network, such as a mobile switching center (MSC) 8, which is coupled to a server 5 providing access to the Internet 24. In operation, the MSC 8 is capable of routing voice and data calls to and from the AED 12, as well as to and from cellular telephones 3 via wireless communication transmissions 2. The AED 12 may be configured to place voice or data calls to a 911 emergency services center 28 via the cellular telephone network 4. Further, the AED 12 may be configured to capture information regarding patient vital signs and diagnostic data, as well as treatments applied to the patient by the AED, and to transmit this data via the cellular telephone network 4 and the Internet 24 to a remote server 26 and/or an emergency response center 28. The AED may also be configured to conduct a voice call (e.g., with a speaker phone) with emergency personnel, such as in an emergency response center 28, or medical personnel via the cellular telephone network 4.

Instead of or in addition to the cellular telephone network 4, the AED 12 may be configured to communicate with another type of wireless communication network, such as an IEEE 802.11 wireless wide area (WiFi) network 14. A typical WiFi network 14 may transmit wireless signals 13 between the AED antenna 76 and a WiFi base station 16 that is coupled to a network gateway server 15 coupled to the Internet 24. Thus, the WiFi network 14 may be used as an alternative connection to the Internet 24 if cellular service is not available, such as may occur when the AED is located within a building. Using network communications via the Internet, the AED can report an activation event either by sending such messages to a remote server 26, or by initiating a VoIP call (e.g., via a VoIP server 26) to an emergency services center 28.

Also as illustrated in FIG. 1, a remote server 26 configured to receive data from the AED 12 may also be configured to communicate received information to an emergency services center 28, or to other medical facility (e.g., a hospital emergency room), via a network connection (e.g., the Internet 24) or a conventional telephone call 27.

Figure 2:
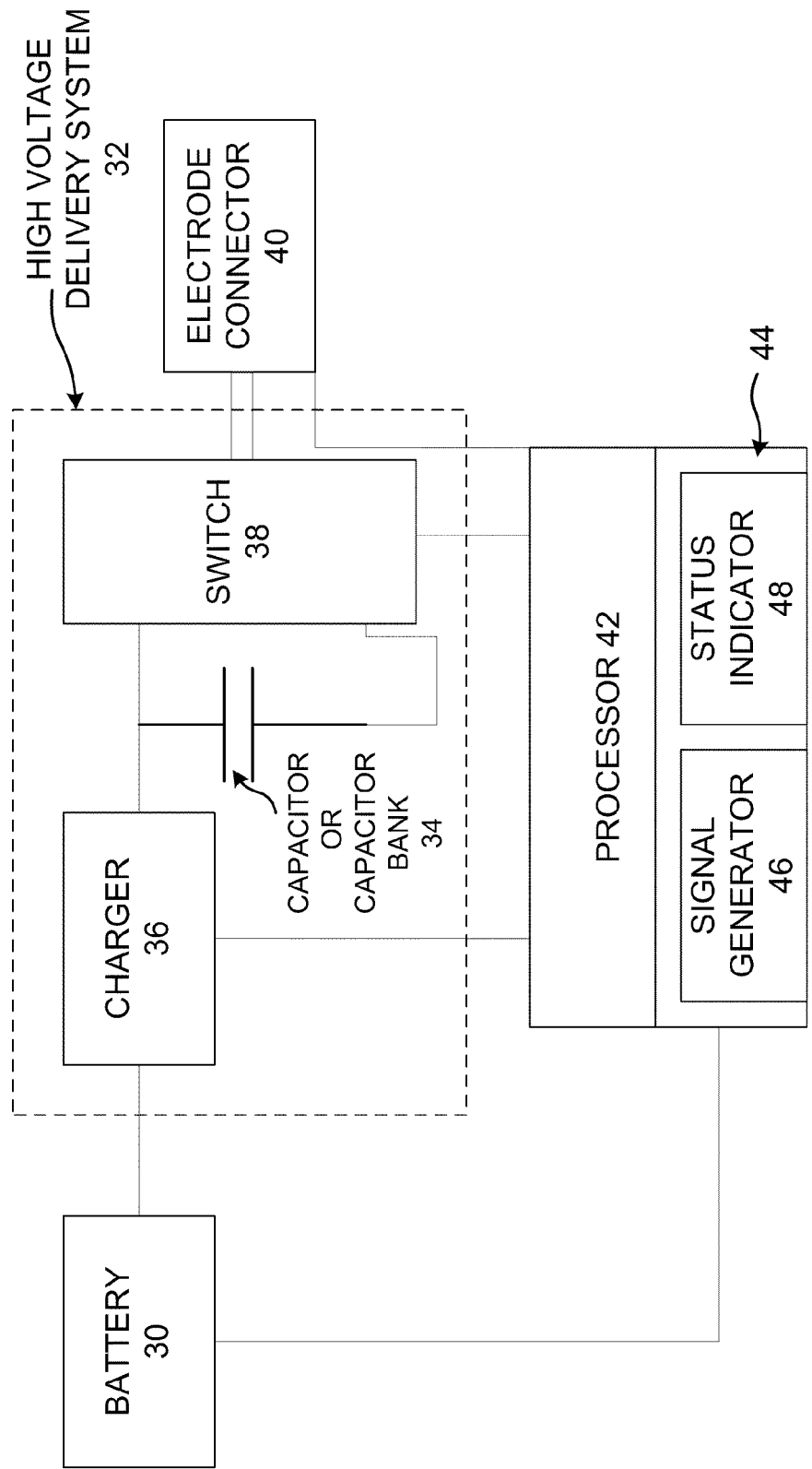
FIG. 2 is a schematic representation of an example conventional AED.

FIG. 2 is a component block diagram of an example conventional AED. A typical AED includes a battery 30, a processor 42, a high voltage delivery system 32 that may include a capacitor or capacitor bank 34, a capacitor charger 36 powered by the battery 30 and a switching mechanism 38, and an electrode connector 40. The processor 42 may be configured to operate the charger 36 and switching mechanism 38 to deliver an electric shock from the capacitor 34 to electrodes (not shown) connected to the electrode connector 40. The AED may include a testing system 44 including a test signal generator 46 and a defibrillator status indicator 48. The testing system can test the operational status of the defibrillator's components and provide an indication of that status (such as with an indicator light) in response to predetermined events or conditions and/or periodically on a preset schedule. The processor in a typical AED is configured to receive and interpret patient vital signs, such as electrical signals emanating from the patient's heart, recognize conditions which require a defibrillation treatment, and to activate the high voltage delivery system 32 so as to apply the appropriate electrical shock to the patient via the electrodes.

Although not illustrated in FIG. 2, a conventional AED may also include a memory coupled to the processor 42 for recording patient vital signs and treatment data, as well as user interface devices, such as an indicator light, a display (e.g., an LCD panel), a microphone for recording ambient noise and a speaker or buzzer for providing audio cues to a caregiver, such as sounds or tones for monitoring the patient's heartbeat.

Figure 3:
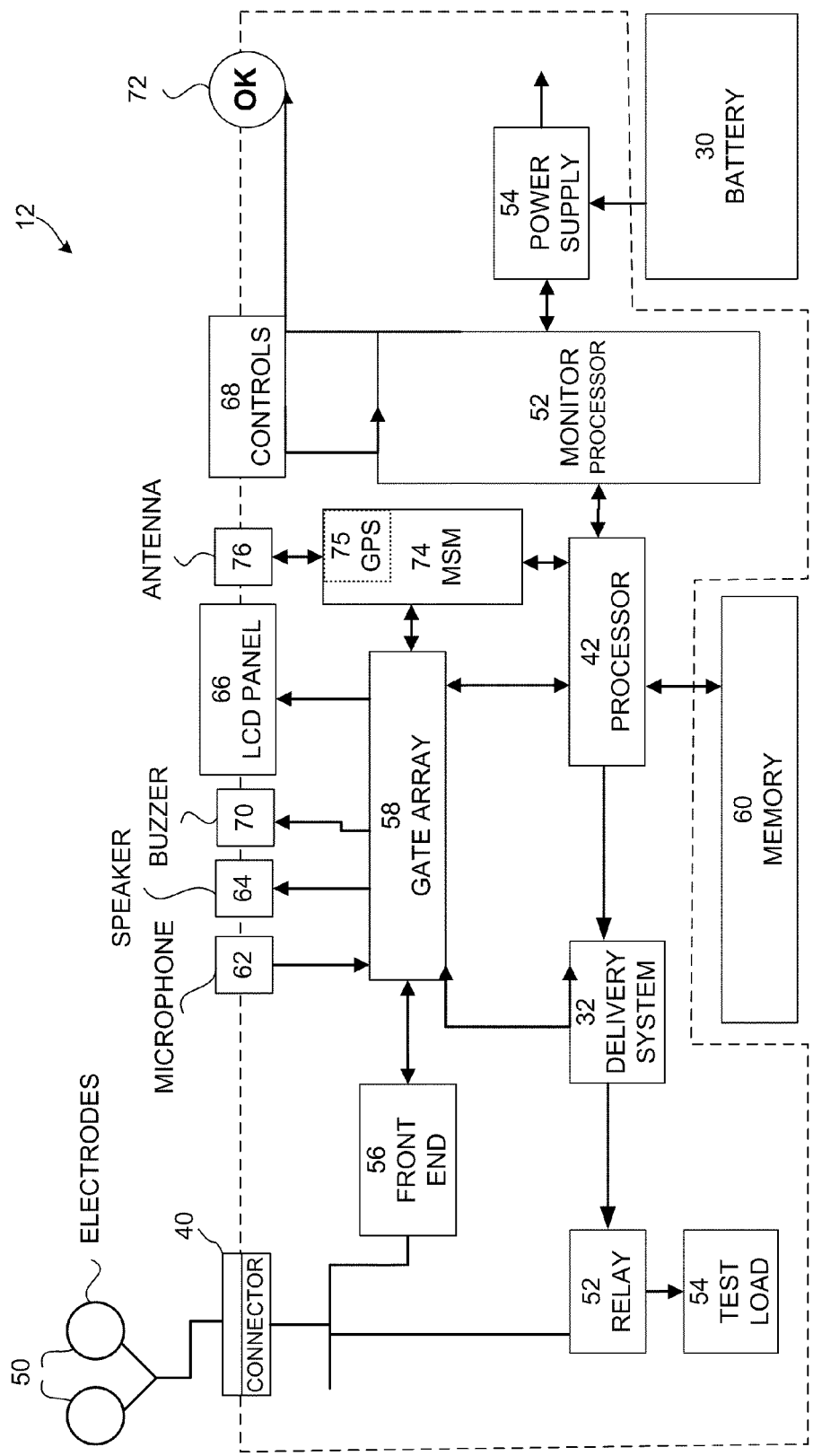
FIG. 3 is a component block diagram of an AED according to an embodiment.

FIG. 3 is a component block diagram of an AED 12 according to various embodiments. The embodiment AED 12 includes components of a conventional AED, as well as a wireless modem 74 (e.g., an MSM) coupled to an antenna 76. Additionally, the AED 12 may include a processor 42 which is configured with software to monitor a patient's heart and activate the defibrillation circuitry as necessary, as well as to perform the functions of the various embodiments. The processor 42 may be a programmable microprocessor and control circuitry, and in some implementations, the processor 42 may include multiple processors, such as one processor for controlling the defibrillation functions and a second processor for controlling other system processes, including the communication processes of the various embodiments. The wireless modem 74 is coupled to the processor 42 and to the antenna 76, and is configured to establish voice and data calls to a cellular telephone network or other type of wireless network. The processor 42 may be configured with software instructions to direct the wireless modem 74 to establish voice or data calls and to transmit data or words that are generated by a voice synthesizer or are stored in memory 60. As explained in more detail below, the processor 42 may recall location information, device identification information, patient data, and treatment data from the memory 60, and may format the information for transmission to a remote server via the wireless modem 74.

In an embodiment, a GPS receiver 75 may be coupled to the antenna 76 and to the processor 42 for providing GPS coordinates (i.e., latitude, longitude and altitude) of the AED. In some implementations, the GPS receiver 75 may be included as part of the wireless modem 74 as illustrated, while in other implementations the GPS receiver 75 may be a separate component.

Power for the AED 12 may be provided by a battery 30 which provides voltage to a power supply circuit 54 that provides power to the other components, including the processor 42 and the high voltage delivery system 32. As described above with reference to FIG. 2, the processor 42 sends control signals to the high voltage delivery system 32 to apply electrical shocks to a patient via the electrodes 50, which are coupled to the AED 12 via a connector 40. In order to provide diagnostic testing of the AED functionality, the high voltage delivery system 32 may be coupled to a relay 52, which can connect to a test load 54 so that the firing of the high voltage delivery system 32 can be accomplished for testing purposes without energizing the electrodes 50.

As described above, the AED 12 must be able to sense patient vital signs and the electrical signals of the patient's heart, essentially functioning as a miniature electrocardiogram (ECG). The signals may be received from the electrodes 50 via the connector 40 by front-end circuitry 56, which may include signal amplifiers and conditioning circuitry, as is well known in the AED arts. Signals received from the front-end circuitry 56 may be provided to the processor 42 for storage in memory 60, as well as for determining an appropriate defibrillation treatment for application to the patient.

In an embodiment, the AED 12 may include other circuitry for communicating with the user, such as: a microphone 62 configured to record ambient noise such as the voice of a caregiver; a speaker 64, which may be used to provide auditory prompts to a caregiver such as sounds or tones indicating the patient's heart beat, as well as to serve as the speaker portion of a speaker phone; other sound generators, such as a buzzer 70 for providing alarms or similar signals to a caregiver; and a display, such as an LCD panel 66.

Control of the user interface devices may be provided by a gate array 58, which may be an application-specific integrated circuit (or another processor) that integrates many of the AED functions, such as display control and many of the instrument control functions. Such a gate array 58 may minimize the number of components within the AED and reduce the processing burden on the processor 42 for user interface tasks. For example, while the processor 42 may control the wireless modem 74 to initiate a voice call, such as to an emergency services center 28, the gate array 58 may serve as the connection between the wireless modem 74 and the microphone 62 and speaker 64, thereby freeing the processor 42 to monitor and treat the patient. Although not illustrated in FIG. 3, the gate array 58 may also include a connection to the memory 64 which can pass stored data to the wireless modem 74 for transmission to a remote server once a data connection has been established under the direction of the processor 42. Similarly, information to be displayed to a user may be provided by the processor 42 to the gate array 58, which then generates the display image presented to the LCD panel 66.

The AED 12 may also include a self-monitoring circuit 52 which performs system monitoring when the AED 12 is in a sleep or low-power condition. The self-monitoring processor 52 may be a separate processor with connections to the various components within the AED 12 that require monitoring, such as the battery 30 and the high voltage delivery system 32. The monitoring processor 52 may be configured to operate when the processor 42 is shut down so as to receive power from the battery or another power source independent of the main processor 42. The monitor processor 52 may activate a status light 72 to indicate that the AED 12 is in satisfactory condition. Results from the diagnostic testing by the self-monitoring processor 52 may be provided to the main processor 42 for transmission to a remote server via the wireless modem 74. The self-monitoring processor 52 may also have its own set of user controls 68, such as a button to initiate a self diagnostic test on command from the user.

While FIG. 3 illustrates three separate processors (i.e., a main processor 42, a monitoring processor 52 and a gate array 58), this is only one possible architecture that may be implemented. Future programmable processors may have sufficient computing power to enable them to perform all functions of the embodiment AED 12. Alternatively, more than three processors may be used in some implementations in order to simplify their design or provide additional reliability. For ease of reference, the embodiments are described herein with reference to a single processor 42, which may be configured with software instructions to perform the various embodiment methods instead of referring to particular coprocessors. This reference to a single processor 42 is not intended to limit the claims to a particular processor architecture, or allocation of functions to particular processor circuits.

Further details regarding the conventional components and functioning of the AED 12 are provided in U.S. Pat. No. 5,879,374 entitled "External Defibrillator with Automatic Self-testing Prior to Use" dated Mar. 9, 1999, the entire contents of which are hereby incorporated by reference.

The wireless modem 74 may be a cellular telephone type transceiver, such as an MSM, which enables the AED 12 to establish a voice or data call via a conventional cellular telephone network. Alternatively, the wireless modem 74 may be another type of wireless modem, such as an IEEE 802.11g wireless wide area WiFi transceiver, which would enable the AED to establish a wireless data link with a WiFi wireless network. In a further alternative, the wireless modem 74 may include both a cellular telephone transceiver and a WiFi transceiver, so that the AED can establish a connection to either type of wireless network, depending upon the signals received when the AED is activated. The wireless modem 74 may also be any type of wireless transceiver that may be developed in the future, including a "White Space" transceiver.

Figure 4:
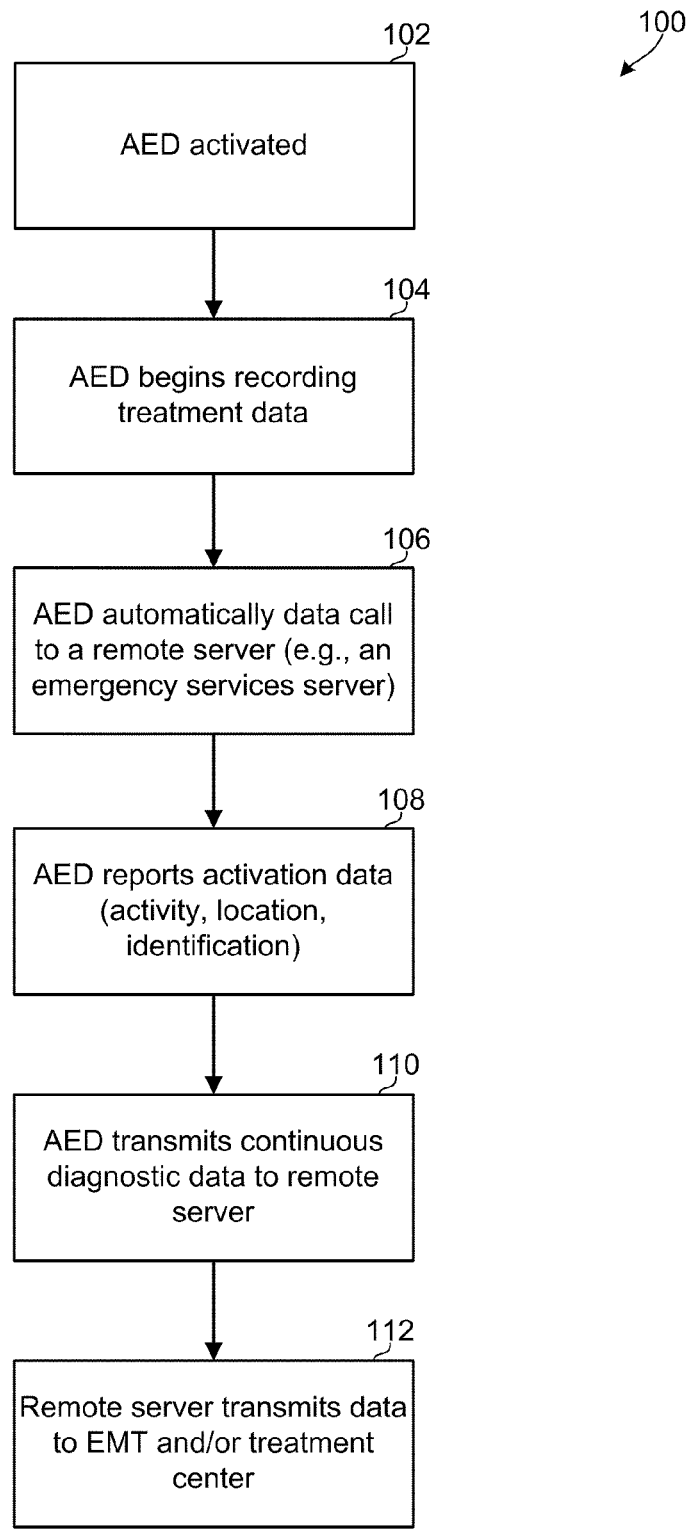
FIG. 4 is a process flow diagram of an embodiment method for automatically placing a data call from an AED to an emergency services center to transmit data.
Figure 5:
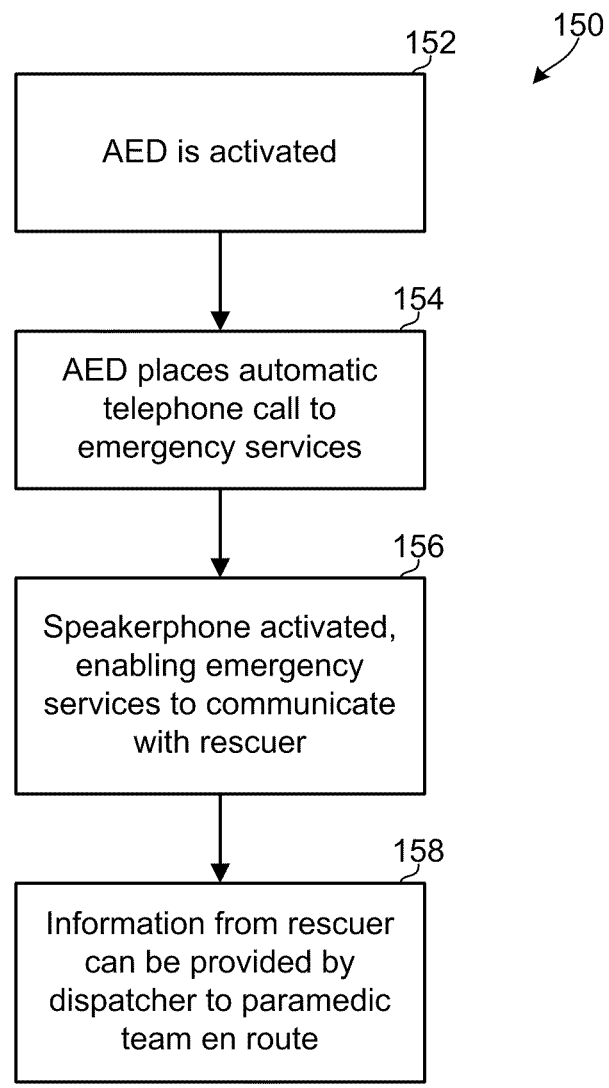
FIG. 5 is a process flow diagram of an embodiment method for automatically placing a voice call from an AED to an emergency services center.

Integrating a wireless modem 74 into the AED 12 enables the system to automatically notify emergency service personnel of the event (i.e., which activation of the AED) and its location, as well as to provide information that may be useful in treating the cardiac victim. Such notification may be accomplished by placing a data call to a remote server and transmitting the data electronically as a data transmission. FIG. 4 provides an overview of processes by which an AED may report an event via a wireless data transmission. Alternatively or in addition, a voice call may be placed to an emergency services center with the notification information provided by a recorded voice or synthesized voice to a 911 operator. If a call is placed to an emergency services center, the connection may be left open after the voice recording has played so that the dispatcher can speak with a caregiver via the built-in speaker phone (i.e., microphone 62 and speaker 64). FIG. 5 provides an overview of processes by which the AED may report an event via an automatic voice call. Even if the event is reported by transmitting data to a server, a voice call can be connected to a dispatcher or other medical personnel via a VoIP connection and a built-in speaker phone.

FIG. 4 shows an overview process 100 of the operation of an AED according to an embodiment in which the emergency notification is accomplished by placing a data call to a remote server via a wireless network. When an AED is activated, step 102, it may begin recording information about the cardiac event for which it is being used, step 104, such as the time of the event, the pulse rate and ECG signals of the patient (once the electrodes are attached), and the number of shocks administered by the AED. Also, when it is activated, the AED automatically activates the wireless modem and places a data call to remote an emergency services server, step 106. The data call sends a report of the AED activation, such as the location and identity of the AED, step 108. In this embodiment, the AED may be configured to report the emergency activation by automatically accessing the Internet via a data call to a cellular data network or WiFi network, and sending data in TCP/IP data packets to a server configured to receive and act upon such emergency announcement data. For example, the AED may be configured to access a server of the emergency services center and transmit data regarding the AED, including information such as an identifier, the location, and the nature of the activation. Alternatively, the AED may be configured to send the event reporting information in other types of electronic formats, including as an e-mail to a particular electronic mail address, or as a Simple Message Service (SMS) message, for example, By reporting the AED activation event electronically, the AED and the receiving computer system can ensure that the location and nature of emergency is accurately recorded, avoiding opportunities for human error. Further, the reporting of the emergency can be made to a server located anywhere in the country, which may then be configured to report the emergency to an appropriate dispatcher based upon current information about the local emergency services. Thus, if the AED is deployed in a location involved in a natural disaster situation, such as an earthquake or hurricane, the emergency call may be handled by a server in an unaffected part of the country. Such a remote server can route the emergency information to individuals or facilities that are able to respond, such as to a temporary dispatcher or an emergency response team by mobile e-mail (e.g., for reception on a Blackberry®) or SMS message (e.g., for reception on a cellular telephone).

In addition to reporting the nature and location of the emergency, the AED may be configured to begin transmitting diagnostic data regarding the ongoing treatment and status of the patient, step 110. The data transmitted via the data call to the remote server may include data that is recorded by the AED in its conventional functioning For example, the AED may transmit to the server the ECG data that it receives via the electrodes attached to the patient, as well as a log of electrical shocks applied to the patient. In this embodiment, the AED can provide information that a treating physician will need for planning the care to be provided to the patient when he/she arrives at the emergency room. The remote server may also be configured to send this diagnostic data directly to onboard computers of a dispatch emergency services team, step 112. Transmitting the data to the dispatched emergency services team can enable the emergency medical technicians to prepare for an immediate response to the patient's condition.

In an embodiment, the remote server may further be configured to begin a VoIP voice call session with the AED which may be configured to enable a speaker phone mode after delivery of the emergency data message. This embodiment may allow a local dispatcher or nurse at a central facility or nearby hospital to begin speaking with the caregiver without requiring the caregiver to pick up a telephone or otherwise stop providing assistance to the victim. In this manner, after the location of the AED has been reliably conveyed to the remote server, the caregiver can be put on the line with a dispatcher, nurse or doctor in order to provide additional information. The remote server may be configured to identify a nearby emergency room and connect a VoIP call between the identified emergency room and the AED so that the caregiver can provide additional information to the facility that will receive the victim.

FIG. 5 is a summary process flow diagram of operations 150 of an AED that reports an activation event via a voice call. When this embodiment AED is activated, step 152, it automatically places a voice telephone call to an emergency services center or local PSAP, step 154, such as by dialing 911. When the voice call is connected, the AED may automatically report the activation event by recorded or synthesized voice, including such information as its present location, the type of activation, its identification number, and any other information that may help an emergency dispatcher to send an appropriate medical response team. For example, the AED may be configured to dial 911, listen for an operator responding to the call, and begin playing a prerecorded announcement of its location and the nature of the emergency, repeating the announcement sufficient times to ensure that an operator will receive the message.

The established telephone call may be continued during treatment of the patient, with the AED further configured to switch to a speaker phone mode after the prerecorded announcement has been repeated a number of times, step 156. This embodiment allows the dispatcher to begin speaking with the caregiver without requiring the caregiver to pick up the telephone or otherwise stop providing assistance to the victim. In this manner, after the location of the AED has been reliably conveyed to the emergency dispatcher, the caregiver can be put on the line in order to provide additional information, such as by responding to questions from the dispatcher. The emergency services dispatcher may then convey information received during the voice call to emergency services teams being dispatched to the scene, step 158.

Figure 6A:
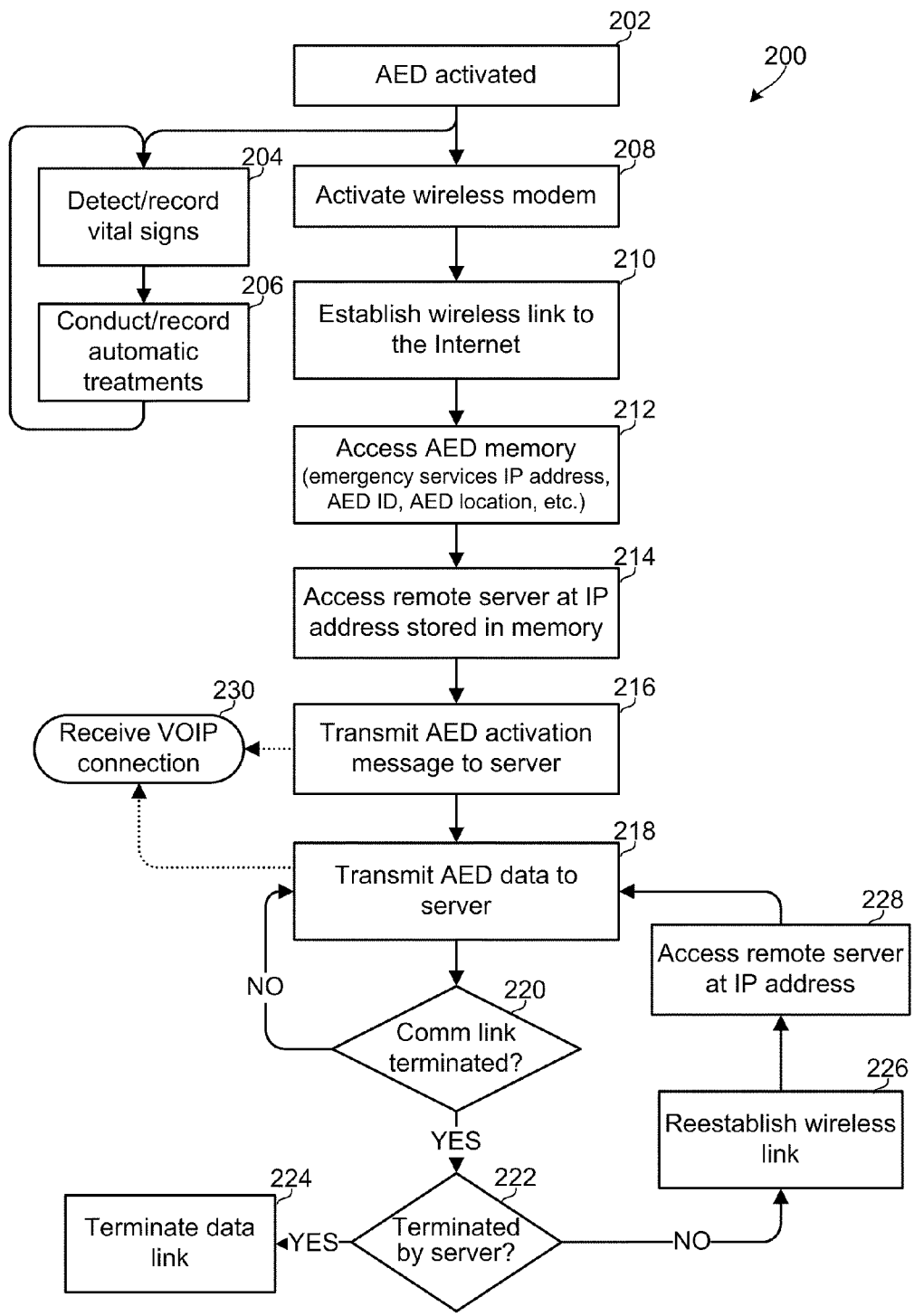
FIGS. 6A-6C are process flow diagrams of embodiment methods for automatically establishing and maintaining wireless voice and data communication between an AED and an emergency services call center.
Figure 6B:
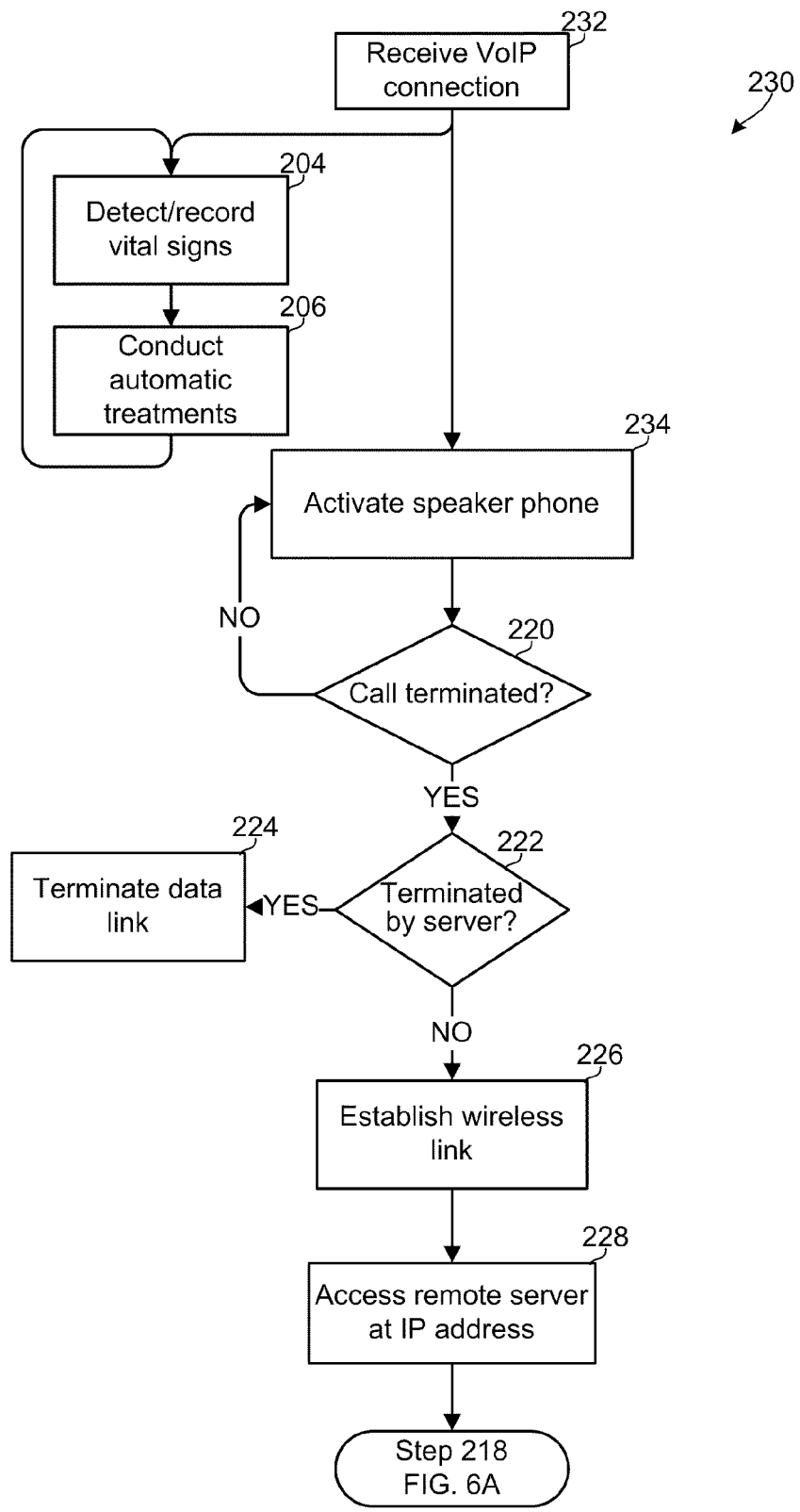
Figure 6C:
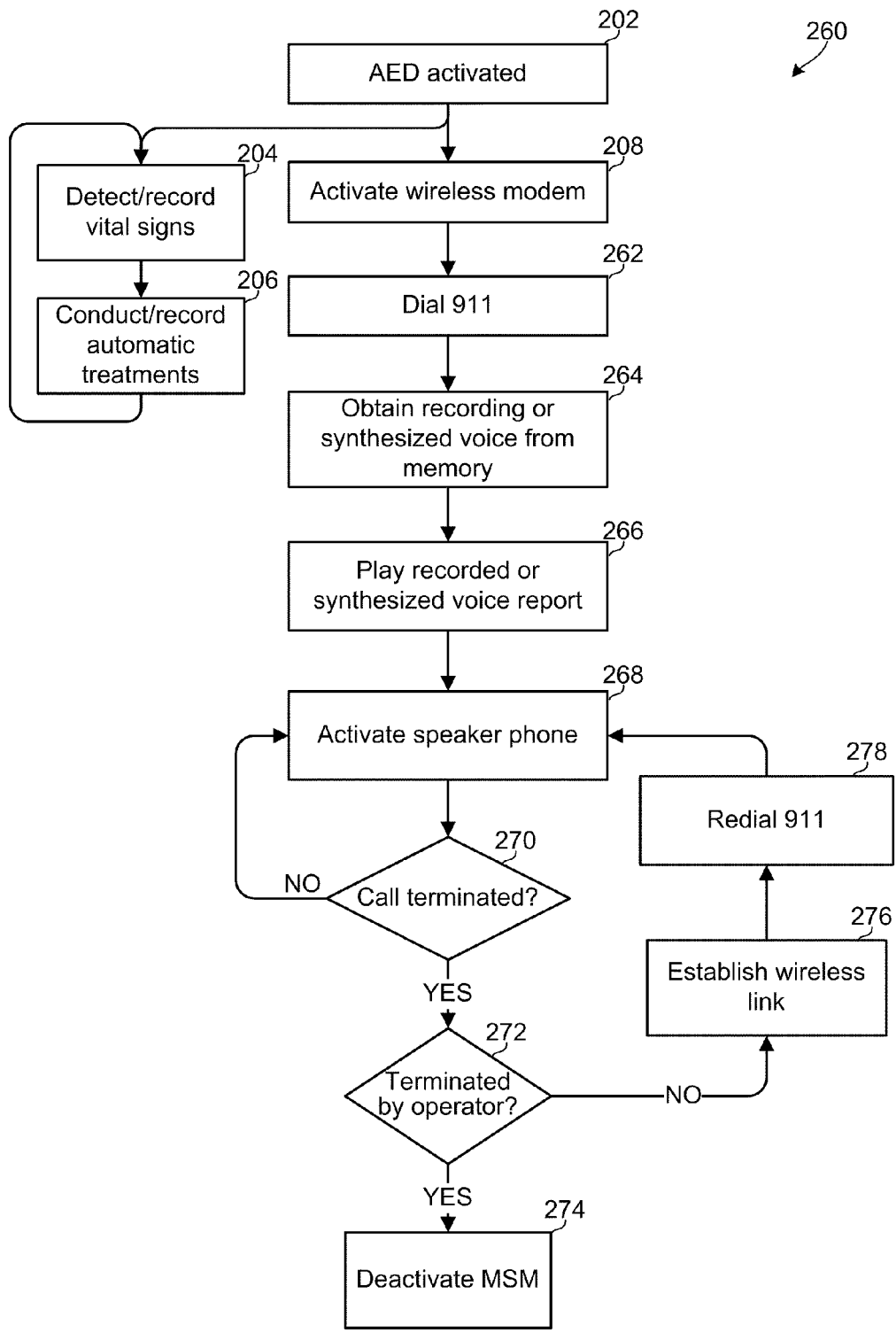

Further details regarding the operations that may be performed by an embodiment of AED are illustrated in FIGS. 6A-6C. FIGS. 6A and 6B illustrate operations that may be performed by an AED that connects to a remote server to report activation and patient data. FIG. 6C illustrates operations that may be performed by an AED that places a voice call to emergency services, such as by dialing 911.

FIG. 6A shows an example process 200 that may be implemented by an AED configured to report activation to a remote server. When not in use, the AED may exist in a sleep mode. When an AED is activated, step 202, its processor 42 begins performing the normal functions of a conventional AED. These normal functions include detecting and recording vital signs picked up by the electrodes 50 when they are attached to the patient, step 204. By analyzing the detected patient vital signs and ECG signals, the processor 42 can determine whether defibrillation treatments are required and, if so, automatically conduct such treatments, step 206. The process of detecting and recording vital signs, step 204, and conducting and recording automatic treatments, step 206, continues until the AED is deactivated, such as by an emergency medical technician.

Concurrent with this conventional operation, an embodiment AED may also activate the wireless modem 74, step 208, and establish a wireless data communication link to an available data network with access to the Internet, step 210. A wireless communication link may be established by automatically placing a data call to a cellular telephone network, logging into a WiFi network (e.g., IEEE 802.11g wireless network), or accessing another form of wireless network that may be deployed in the future. In an embodiment, the wireless modem 74 may be configured with multiple types of wireless transceivers (e.g., both a cellular telephone transceiver and a WiFi transceiver), and the AED processor 42 may be configured to determine which type of network signals can be received, and select for use the type of network that will provide the most reliable connection at the time and location of the AED activation.

Before, during, or after accessing the Internet via a wireless data network, the AED processor 42 may access data in memory to enable it to report the activation event and its current location to a remote server, step 212. For example, the IP address of the remote server that the AED should access to report the activation event may be stored in memory, along with the AED identifier and location information that should be included in an activation report message. As part of this process step 212, the AED processor 42 may also access an integrated GPS receiver 75 to obtain current location information in the form of GPS coordinates. Obtaining present location information enables the AED to accurately report its location when the device has been moved from its usual storage location, such as to reach a victim outside a building. Including a GPS receiver 75 in the AED also enables the accurate reporting of the activation location by devices that are normally stored in vehicles, such as buses, trains, ferries, and aircraft.

Using the IP address obtained from memory, the AED processor 42 may access a remote or centralized server, step 214, such as, for example, a server of a nearby emergency services center. Upon accessing the remote server, the AED processor 42 may authenticate itself to the server, such as by exchanging credential information stored in memory, so that the server can confirm that the AED is authentic and that an emergency activation report from it can be trusted. Additionally, the wireless modem 74 and the remote server may negotiate an encrypted communication link, such as an secure socket link (SSL) connection, so that the emergency location and patient data can be protected from eavesdropping.

Once a TCP/IP communication link is established with the remote server, the AED may automatically transmit to the server data regarding the AED activation, step 216. This activation data may include, but is not limited to, the location of the AED, the nature of the activation, a sensed condition of the patient (e.g., whether ECG data is available and whether a cardiac arrest condition is detected), and other information that may enable a dispatcher to initiate an appropriate response. The remote server may confirm receipt of the activation message and the AED processor 42 may be configured to continue to transmit the activation message until an acknowledgment is received from the remote server. As mentioned above, instead of establishing a TCP/IP link to a remote server, the activation message may be transmitted as an e-mail or other form of addressable message that can be reliably delivered to a destination computer.

Once the AED activation has been reported so that emergency personnel can be routed to the AED's location, the established communication link with the remote server may be used to establish a VoIP connection, process 230 described below with reference to FIG. 6B, or to transmit patient diagnostic and treatment data to the server, step 218. The AED may be configured to continuously push data regarding the ongoing treatment and status of the patient from the AED to the remote server during the treatment of a patient. The patient diagnostic and treatment data may be transmitted continuously as it is received and stored by the AED. Alternatively, the AED may be configured to periodically transmit such data in packets or blocks. Transmitting data periodically may enable the open communication link to the remote server to be used for other communications, such as establishing a parallel VoIP connection, process 230.

In addition to transmitting diagnostic and treatment data, the AED may continue to report its current location as determined by an integral GPS receiver 75. This information may be vital in a situation in which the victim is on a moving vehicle, such as a bus or ferry. By continuing to transmit location information, emergency response personnel can be redirected to the victim's current location upon arrival on scene.

In another embodiment, the AED monitors the status of the wireless connection, since wireless communication links are frequently subject to disruption due to weak signal strength or interference, as may occur within a building. In this embodiment, the AED processor 42 may be configured to monitor the communication link and reestablish a link to the remote server if communications are inadvertently terminated. If the call is dropped or terminated without an action by the operator of the AED or the remote server, the AED may be configured to automatically re-establish the wireless link and re-place the data or voice call. For example, the processor 42 may periodically determine whether the communication link has been terminated, determination 220. If the communication link is still established (i.e., determination 220="No"), the processor 42 may continue to transmit patient and treatment data to the remote server, step 218. However, if the communication link has been terminated (i.e., determination 220="Yes"), the processor 42 may determine whether the communication link was terminated by the server which would indicate that the termination was not inadvertent, determination 222. This determination may be made by inspecting a last communication received from the server to determine whether it involved a communication link termination message. If the processor 42 determines that the server terminated the communication link (i.e., determination 222="Yes"), the processor 42 may instruct the wireless modem 74 to terminate the data link and shut down, step 224. However, if the processor 42 determines that the server did not terminate the communication link (i.e., determination 222="No"), the processor 42 may direct the wireless modem to reestablish a wireless communication link to the Internet, step 226, and use that connection to access the remote server at its IP address, step 228. Once the call connections have been re-established, the AED processor 42 may continue the transmission of patient and treatment information from the AED to the remote server, step 218.

For AED embodiments that include a speaker 64 and microphone 62 to enable a speaker phone operation, the open communication link with the remote server can be used to initiate a VoIP voice connection between an appropriate medical or emergency services person and the caregiver. FIG. 6B shows a process 230 that may be implemented in an AED to conduct a voice call via a VoIP connection. With a communication link established between the AED and a remote server, the remote server can initiate a VoIP call from the AED to an appropriate person such as an emergency services dispatcher at a local PSAP or a nurse within a nearby emergency room facility. The AED processor 42 may be informed of the VoIP connection in a message received from the remote server, step 232. In response, the processor 42 may activate a VoIP application to receive and process voice data in IP format, and direct audio signals to the speaker 64 and receive sound from the microphone 62, step 234. As mentioned above, the speaker phone operation using a VoIP connection can enable a caregiver to provide additional information, or receive instructions from emergency dispatcher medical personnel, without having to pause efforts to help the patient. While the voice call with the emergency services dispatcher or other personnel proceeds the AED simultaneously continues treatment operations by detecting and recording vital signs, step 204 and conducting automatic treatments, step 206, until the AED is deactivated.

As mentioned above, since wireless communication links may be dropped inadvertently, an embodiment of the AED may be configured so that the processor 42 periodically determines whether the communication link that is the basis of the VoIP call has been terminated, determination 220. If the communication link is still established (i.e., determination 220="No"), the processor 42 may continue the speaker phone operation, step 234. However, if processor 42 determines that the communication link has been terminated (i.e., determination 220="Yes"), the processor 42 may determine whether the communication link was terminated by the server. which would indicate that the termination was not inadvertent, determination 222. This determination may be made by inspecting a last communication received from the server to determine whether it involved a communication link termination message, such as a VoIP call termination message. If the processor 42 determines that the server terminated the communication link (i.e., determination 222="Yes"), the processor 42 may instruct the wireless modem 74 to terminate the data link, step 224. However, if the processor 42 determines that the server did not terminate the communication link (i.e., determination 222="No"), the processor 42 may direct the wireless modem to reestablish a wireless communication link to the Internet, step 226, and to use that connection to access the remote server at its IP address, step 228. Once the communication link to the remote server is reestablished, communications between the AED and the remote server may proceed as described above with reference to step 218 in FIG. 6A. For example, the remote server may reestablish a VoIP call connection, in which case it would inform the AED of such a call, step 232, in process 230 as described above. If a VoIP call is reestablished, the voice call between the AED operator and the emergency services dispatcher or medical personnel can continue as before.

In operation, information obtained by a dispatcher from either the voice or data call from the AED may be forwarded by the dispatcher to an ALS team en route to the site of the emergency and/or to an emergency room or cardiac center that will receive victim, for instance.

FIG. 6C shows a process 260 that may be implemented in an AED embodiment configured to place a voice call, rather than a data call to a remote server. When the AED is activated, step 202, it may begin the conventional operations of detecting and recording patient vital signs, step 204, and conducting and reporting automatic treatments, step 206. Simultaneously, the AED processor 42 may activate the wireless modem and access a cellular telephone network, step 208. Once the cellular telephone service is established, the processor 42 may cause the wireless modem to dial an emergency services center, such as by dialing 911, step 262. In conjunction with placing the call to emergency services, the processor 42 may obtain a recording (e.g., a .wav file) or synthesized voice message from memory to be used in announcing the AED activation event to a dispatcher, step 264. As part of this step, the AED processor 42 may be configured to receive location information from an integral GPS receiver 75 and translate that information into synthesized voice sounds so that the AED can also verbally report accurate location information to a dispatcher. The processor 42 may be configured to listen for an operator voice, and when detected, begin playing the recorded and/or synthesized voice report, step 266. The recorded and/or synthesized voice report may be repeated a number of times to ensure that a dispatcher can accurately record the information concerning the AED location, the nature of the activation event and other prerecorded information that may be useful to an emergency services dispatcher. Once the recorded and/or synthesized report has been played the preset number of times, the processor 42 may connect the speaker 64 and microphone 62 to the wireless modem 74 to initiate a speaker phone voice call, step 268. In this manner, the emergency services dispatcher can obtain further information from the caregiver, without requiring the caregiver to interrupt efforts to assist the patient.

Similar to the embodiments described above with reference to FIGS. 6A and 6B, in process 260 the AED processor 42 may be configured to periodically determines whether the voice call has been terminated, determination 270. If the communication link is still established (i.e., determination 270="No"), the speaker phone operation may continue, step 268. However, if the processor 42 determines that the communication link has been terminated (i.e., determination 270="Yes"), the processor 42 may determine whether the telephone call was terminated by the AED operator or the emergency services dispatcher, which would indicate that the termination was not inadvertent, determination 272. This determination may be made by inspecting the call log to determine whether the link was lost rather than being terminated as a result of a hang up at one end or the other. If the processor 42 determines that an operator terminated the communication link (i.e., determination 272="Yes"), the processor 42 may deactivate the wireless modem, step 274. However, if the processor 42 determines that the call was terminated by a dropped communication link (i.e., determination 272="No"), the processor 42 may direct the wireless modem to reestablish a link to the cellular telephone network, step 276, and redial 911, step 278. Once a call to emergency services is reestablished, the speaker phone call may continue, step 268.

As mentioned above, after an AED treatment event is concluded, the patient and treatment data from the event that was stored in memory is typically downloaded to a computer of the AED manufacturer or service provider, and/or to a computer system of the institution whose ALS team responded to the emergency (e.g., hospital, fire station, police station, etc.) Downloading the most recent treatment information can enable accurate patient record-keeping. Also, an AED may be designed to store only one patient's treatment information at a time, which means that the most recent treatment information stored in the AED's memory must be downloaded before the AED can be used again. Manual downloading of information stored in the AED may be a distraction in a busy trauma center such as an urban fire station or hospital.

Figure 7:
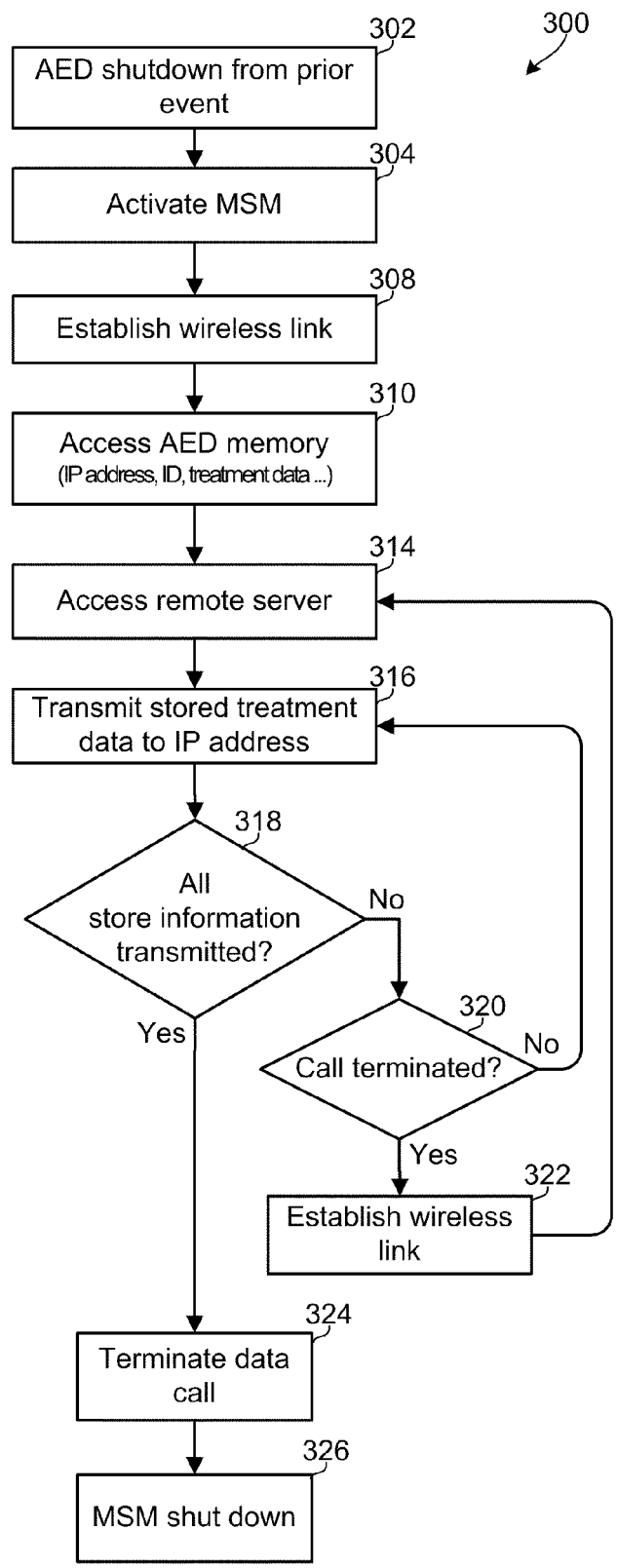
FIG. 7 is a process flow diagram of an embodiment method for wirelessly transmitting AED usage data to a remote server.

In an embodiment, the AED may be configured to wirelessly transmit information regarding the last use of the AED to a remote server for storage and use. The remote server may be the computer system of the responding agency that provided an ALS team, a server of the emergency services center, or a server of the AED manufacturer or servicing company. FIG. 7 shows a process 300 by which an embodiment AED can transmit the stored treatment information to a remote server via a wireless communication link. When the AED is shutdown or deactivated from a usage event, step 302, the processor 74 may activate the wireless modem, step 304, so that the wireless modem can establish a communication link to a wireless data network, step 308. As described above, the wireless modem 74 may be configured to establish a data communication link with a variety of different types of networks, such as a cellular telephone data network or a WiFi network, and may make a network selection based upon sensed signal strengths. The processor 42 may access memory to obtain an IP address for a remote server to which the data should be transmitted, along with information to be transmitted, such as the AED identifier and the patient and treatment data, step 310. Using the information obtained from the memory, the AED processor 42 causes the wireless modem to access the appropriate remote server, step 314, and begin transmitting the stored treatment data to the server, step 316. The processor 42 may be configured to monitor the information downloading to determine when all of the information has been transmitted, determination 318. This determination may be made by comparing the information that has been transmitted to the total amount of information stored in memory or by checking status flags or pointer values involved in the information downloading process. Once all of the stored information has been transmitted (i.e., determination 318="Yes"), the processor may inform the remote server that the download is complete and direct the wireless modem to terminate the data call, step 324.

As with other embodiments, the AED processor 42 may monitor the status of the wireless connection to determine if the call is dropped or terminated, determination 320. So long as the wireless communication link remains established (i.e., determination 318="No") and more information remains to be transmitted (i.e., determination 318="No"), the processor 42 may continue to transmit the stored patient and treatment data to the remote server, step 316. If the processor 42 determines that the wireless connection has been terminated (i.e., determination 320="Yes") before all information has been transmitted (i.e., determination 318="No"), the processor may direct the wireless modem to automatically re-establish the wireless communication link, step 322, and re-access the remote server, step 314. Once the communication link to the remote server has been re-established, the AED continues transmittal of the patient and treatment data from the AED memory to the remote server, step 316.

AEDs must be serviced periodically to ensure that they remain in working order. A conventional AED has the ability to run periodic self-testing programs to identify internal problems, such as a low battery charge. The conventional AED will display some indication that servicing is needed, such as a status light or periodic tone. The custodian of the conventional AED must then place a service call to the manufacturer or other servicing organization to come and service the AED. The service indicator may not be immediately noticed by the owner of the AED, particularly if the service indicator is a modestly-sized visual indicator. An AED may therefore need servicing for some time before a service call is placed by the owner, either due to delays by the owner or failure to notice that servicing is needed. This delay in servicing may mean that the AED is not available for use when needed.

Figure 8:
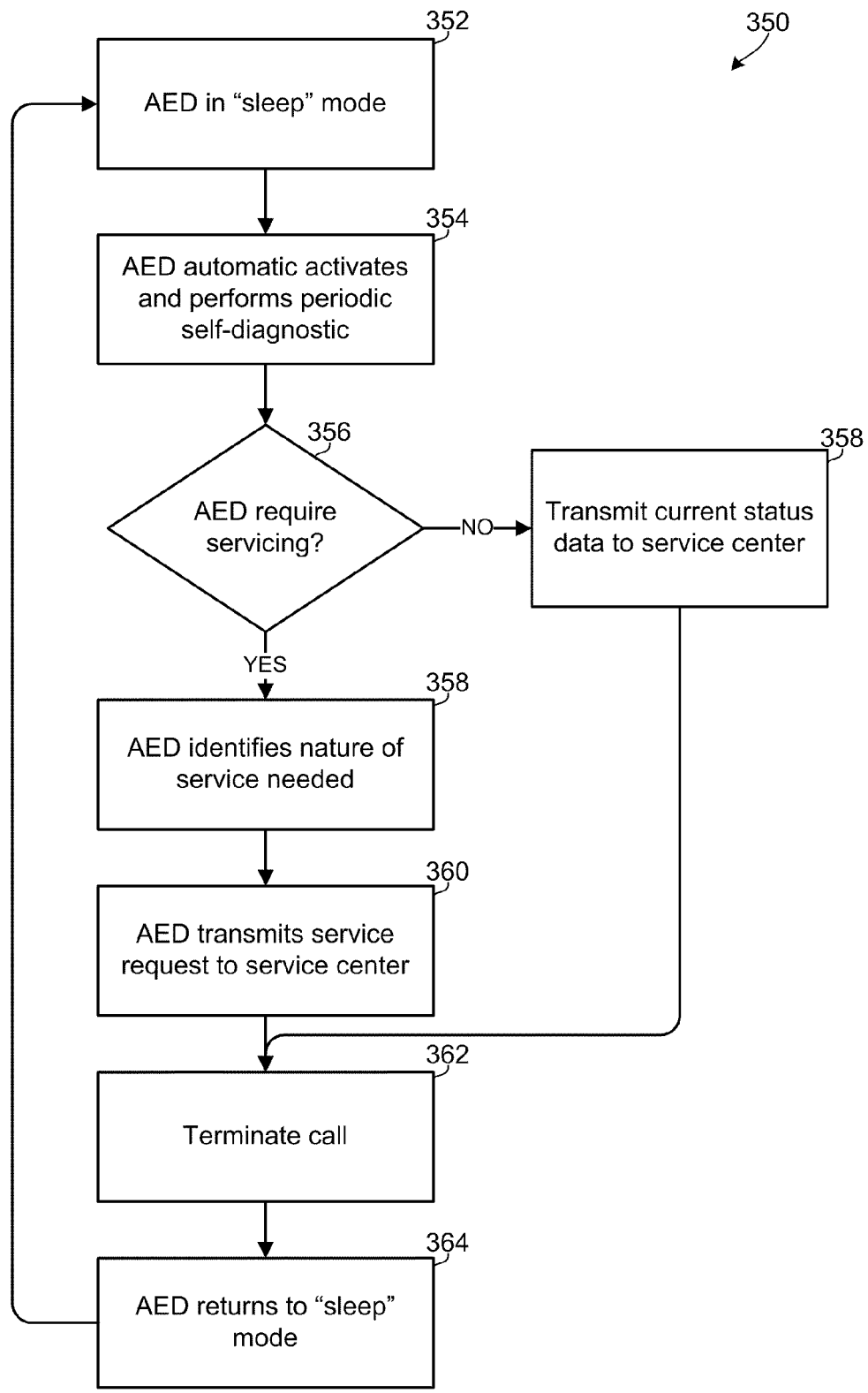
FIG. 8 is a process flow diagram of an embodiment method for wirelessly transmitting status and diagnostic information to a remote service center.

In an embodiment, an AED can use the integral wireless modem to automatically transmit the results of periodic self-testing to a servicing center via a wireless communication link. FIG. 8 shows a process 350 by which an AED may automatically transmit self-diagnostic data according to an embodiment. The AED may be in "sleep" mode when not in use, step 352. While in sleep mode, the AED, or a portion of the AED (e.g., a separate monitoring processor 52), automatically activates and performs periodic self-diagnostic tests according to a pre-set schedule, step 354. At the conclusion of a self-diagnostic test, the AED processor 42 or monitoring processor 52 may determine whether servicing is required, determination 356. If the processor 42 or monitoring processor 52 determines that no service is required (i.e., determination 356="No"), the AED may activate the wireless modem to establish a communication link to a remote server, and wirelessly transmit the self-diagnostic test data to the remote server, such as a server at a service center, step 358. Once the diagnostic data has been transmitted, the processor 42 or monitoring processor 52 may terminate the wireless communication link, step 362, and return to the "sleep" mode, step 364.

If the processor 42 or monitoring processor 52 determines that servicing is required (i.e., determination 356="Yes"), the AED processor 42 or monitoring processor 52 may determine the nature or type of servicing that is needed, step 358, activate the wireless modem to establish a communication link to a remote server, and wirelessly transmit a service request message to the remote server, step 360. After transmitting the service request, the AED processor 42 or monitoring processor 52 terminates the data call, step 362, and returns to "sleep" mode, step 364.

The embodiment described above with reference to FIG. 8 enables the AED to report when it is no longer operable so that service teams can quickly repair or replace the unit. Also, by periodically reporting self diagnostic test results, such as battery charge level, an AED service provider can anticipate when a service call should be made to service or replace the AED unit. Thus, this embodiment should reduce the cost of maintaining AED devices in a number of locations as well as increase the likelihood that the AED will be functional when activated in an emergency situation.

In an alternate embodiment, the AED may be configured to receive a data call from a remote servicing center server and establish a data connection that enables the remote servicing center to request the AED to perform a self-diagnostic evaluation. In this embodiment, a data call may be placed from a remote server located at an AED service center to an AED by dialing the cellular telephone number of the wireless modem. The AED processor 42 and the wireless modem 74 may be configured to accept incoming calls from certain telephone numbers (e.g., the telephone number of a known service provider) or VoIP calls from certain IP addresses, and establish a communication link (i.e., voice or data link) with the calling server. Once the connection is established, a command may be sent from the remote server and received by the AED processor 42, such as a command to perform a diagnostic self-test. When such a command is received, processing by the AED processor 42 or monitoring processor 52 may proceed as described above with reference to FIG. 8 so that the self-diagnostic test results can be transmitted to the remote server. This embodiment enables AED service providers to confirm the current status of their AED units and to check the effectiveness of an AED's self-testing function.

Figure 9:
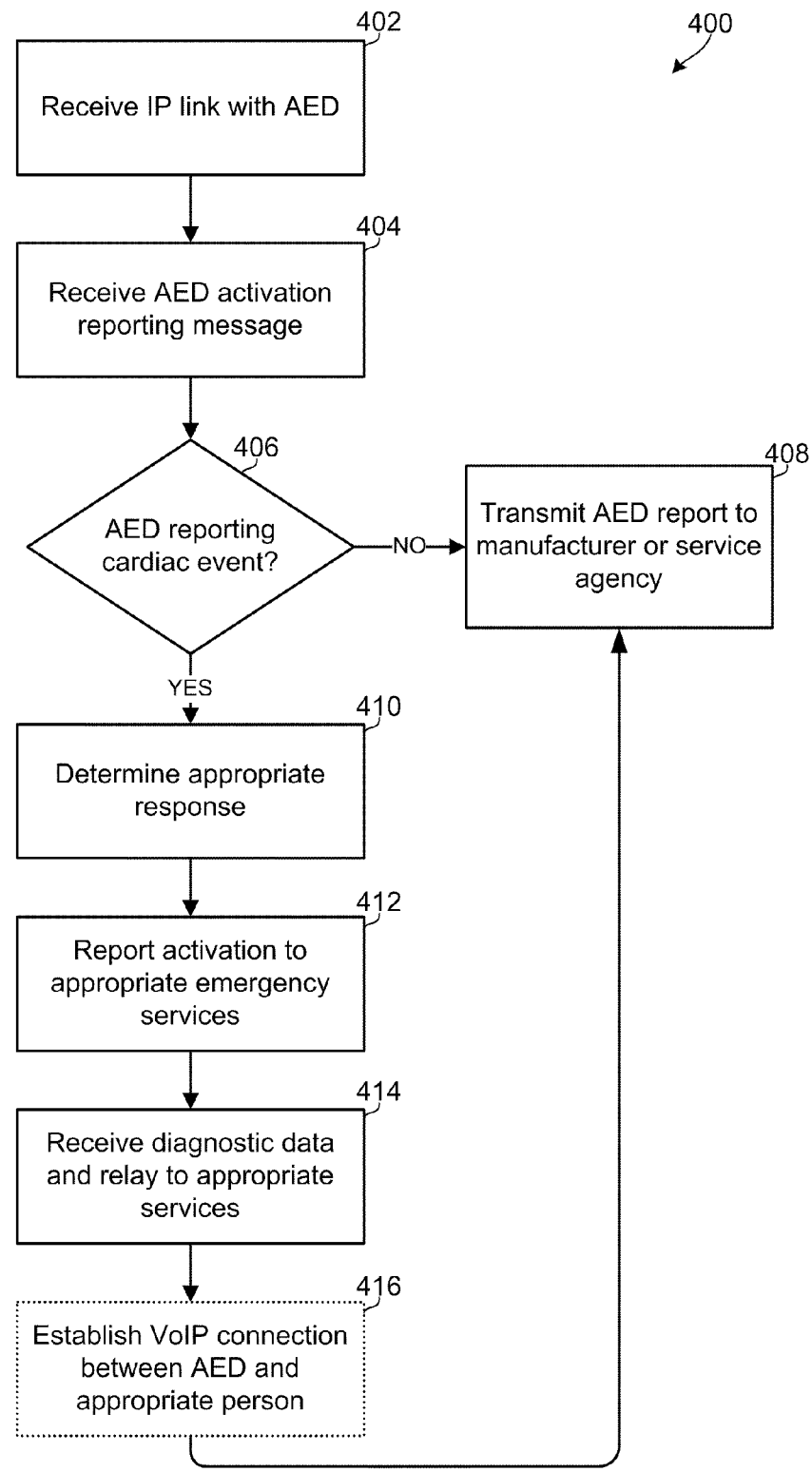
FIG. 9 is a process flow diagram of an embodiment method for receiving and responding to an AED activation message.

FIG. 9 illustrates a process 400 that may be implemented within a remote server to process an AED activation message received via a wireless data call. As described above with reference to FIG. 6A, an embodiment AED may be configured to automatically report activation of the unit to a remote server in a data message sent via a wireless data link. A remote server may be informed of an incoming message from an AED when it receives a TCP/IP link establishment message, such as a request to establish an SSL link, step 402. The remote server may cooperate with the AED to negotiate and establish a communication link, and then received the AED activation reporting message, step 404. As part of establishing a communication link with the AED, the remote server may request and analyze authentication information such as encrypted credentials to enable it to confirm that the AED is a trusted device and that an activation message from it can be trusted.

The remote server may parse the received activation reporting message to determine whether the message is reporting a cardiac event, determination 406. This determination may enable the receiving server to distinguish between an inadvertent activation, a service call activation, and an actual cardiac emergency. The AED may include information regarding the activation, such as whether the electrodes 50 have been deployed, and/or whether patient ECG information is being received. If the server determines that the AED activation report does not involve a cardiac event (i.e., determination 406="No"), the server may transmit the AED activation report to the AED manufacturer or a service provider that tends to the particular AED unit, step 408. Reporting such activation may enable the manufacturer or service provider to confirm a service call or determine that the AED unit should be serviced to determine if it has been damaged by an inadvertent activation.

If the server determines that the AED activation report does involve a cardiac event (i.e., determination 406="Yes"), the server may use the information received in the activation report to determine the appropriate response, step 410. This determination may involve identifying the proper emergency services center to notify based upon the location and identifier of the AED. The response may also involve notifying an emergency room or cardiac critical center that is located closest to the AED so that medical staff is notified at the earliest possible moment. The appropriate response may also depend upon the time of day and day of week in order to take into consideration typical traffic patterns, hours of operation of medical facilities, and protocols that depend upon such temporal variables. Additionally, the server may evaluate any patient diagnostic information included in the notification message, such as raw ECG data or conclusions reached by the AED in its own evaluation of the patient data. For example, the server may be configured to initiate different responses based upon whether the patient is exhibiting cardiac arrest, severe fibrillation, moderate or intermittent fibrillation, or normal ECG patterns. Enabling different responses to patient situations may enable the server to initiate more responsive, cost effective or reliable responses to the patient's particular situation.

Based upon the determined appropriate response, the server may report the AED activation event to the appropriate emergency services center or dispatcher, step 412. This report may be accomplished by sending a TCP/IP message or another type of addressable message, such as an e-mail, to a server in the appropriate organization. Alternatively, the server may store a record to a database that is accessed by a server in the appropriate organization and used to generate displays and notices to the emergency services personnel. The organization receiving the report from the server can use the information to dispatch an ALS team to the AED reporting the activation, as well as to notify an emergency room that the patient will be incoming.

In parallel or after notifying the appropriate emergency services center of the emergency, the server may begin receiving patient diagnostic and treatment information from the AED via the open communication link, step 414. Depending upon the determined appropriate response, the server may relay the received data to an appropriate organization, such as the ALS team in route to the victim and/or the emergency room that will receive the patient. The server may route the receive patient and treatment data via a series of TCP/IP messages, via a series of e-mail messages, as a data stream via the Internet or via other known Internet communication technology. The server may also post the receive data to one or more databases that may be accessed by medical team computer systems, such as by an emergency room server, as well as by a server of an AED manufacturer or service provider. The distribution of the received data may be part of the appropriate response determined in step 410.

Additionally or alternatively, the server may set up a VoIP call between the AED and an appropriate person, such as an emergency service dispatcher or a doctor or nurse within the emergency room that will receive the patient, step 416. To set up the VoIP call, the server may activate a VoIP application to enable it to convert encoded sound data received from the AED into sound that is transmitted in a telephone call to a human operator and convert voice sound from the operator into encoded sound data for transmission to the AED via the open communication link. Alternatively, the server may redirect the open communication link to another server configured to conduct VoIP calls. The telephone number to be called to establish the VoIP call may be determined as part of the appropriate response determined in step 410.

In an embodiment, the server may be configured to conduct the VoIP call with the AED at the same time that it receives patient and treatment data from the AED. This may be accomplished by configuring the AED to identify data packets containing VoIP information or patient/treatment data so that the server can recognize and parse the packets appropriately. In this manner, the AED can transmit patient/treatment data in packets in between VoIP data packets.

Once the data communication link to the AED is terminated, the server may report the AED activation to the AED manufacturer and/or an AED service provider, step 408. This reporting may be made by sending a TCP/IP message, email, or other type of electronic communication to a server of these organizations. This reporting may also include some information regarding the treatments provided, if such information is of value in designing, maintaining or monitoring the performance of the AED.

As mentioned above, the server to which the AED establishes a communication link may be located anywhere, including within an emergency services center, a hospital, an AED manufacturer, an AED service provider, or a third party. Additionally, the AED may be configured to attempt to access a number of alternative servers, to reduce the chance that problems with a particular server or communication links to the server prevent the AED from completing the automatic reporting.

Figure 10:
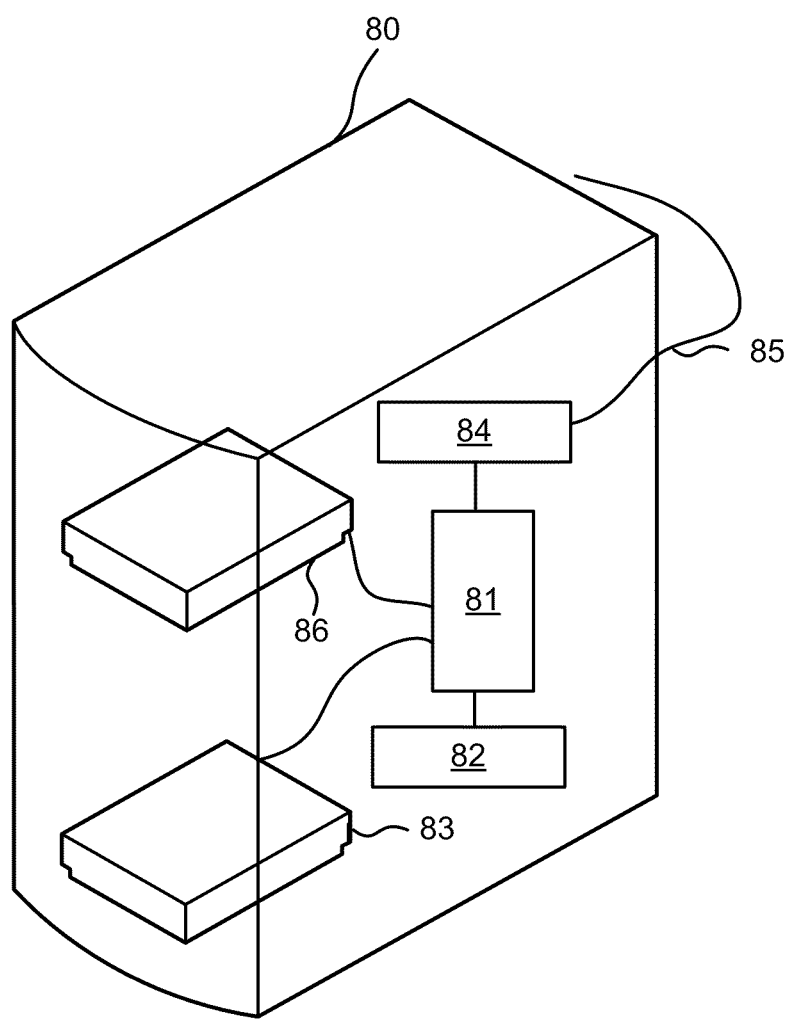
FIG. 10 is a component block diagram of an example remote server suitable for use in the various embodiments.

The embodiments described above may be implemented with any of a variety of remote server devices, such as the server 80 illustrated in FIG. 10. Such a server 80 typically includes a processor 81 coupled to volatile memory 82 and a large capacity nonvolatile memory, such as a disk drive 83. The server 80 may also include a floppy disc drive and/or a compact disc (CD) drive 86 coupled to the processor 81. The server 80 may also include a number of connector ports 84 coupled to the processor 81 for establishing data connections a network 85, such as the Internet.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The AED hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. References to a processor herein are intended to refer to a general-purpose processor such as a microprocessor, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary embodiments, the functions described may be implemented in hardware, software, firmware, or any combination thereof. If implemented in software, the functions may be stored as one or more instructions or code on a non-transitory computer-readable medium. The steps of a method or algorithm disclosed herein may be embodied in a processor-executable software module executed which may reside on a non-transitory computer-readable medium. Non-transitory computer-readable media includes both computer storage media and communication media including any medium that facilitates transfer of a computer program from one place to another. A storage media may be any available media that may be accessed by a computer. By way of example, and not limitation, such non-transitory computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of non-transitory computer-readable media. Additionally, the operations of a method or algorithm may reside as one or any combination or set of codes and/or instructions on a non-transitory machine readable medium and/or non-transitory computer-readable medium, which may be incorporated into a non-transitory computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. An automatic external defibrillator (AED), comprising:
a processor;
a mobile station modem coupled to the processor; and
an antenna coupled to the processor,
wherein the processor is configured with processor-executable instructions to perform operations comprising:
establishing a first communication link with a cellular data network via the mobile station modem and accessing an Internet via the established first communication link upon activation of the AED;
accessing a remote server via the Internet using the first communication link;
communicating an AED activation message to the remote server via the Internet using the first communication link;
establishing a second communication link with the cellular data network via the mobile station modem and accessing the Internet via the established second communication link upon deactivation of the AED;
accessing the remote server via the Internet using the second communication link; and
communicating patient diagnostic data to the remote server via the Internet using the second communication link.

2. The AED of claim 1, wherein the processor is configured with processor-executable instructions to perform operations further comprising:
placing a placing a cellular telephone call to an emergency services center; and
communicating a verbal message stored in memory identifying a location of the AED.

3. The AED of claim 2, further comprising:
a speaker coupled to the processor; and
a microphone coupled to the processor,
wherein the processor is configured with processor-executable instructions to perform operations further comprising:
operating the speaker and the microphone as a speaker phone to enable a voice call with the emergency services center.

4. The AED of claim 3, wherein the processor is configured with processor-executable instructions to perform operations further comprising:
receiving and processing voice-over-IP (VoIP) message packets; and
conducting a VoIP voice call via the established first communication link while operating the speaker and the microphone as the speaker phone.

5. The AED of claim 1, wherein the processor is configured with processor-executable instructions to perform operations such that the remote server is an emergency services center server.

6. The AED of claim 1, wherein processor is configured with processor-executable instructions to perform operations further comprising:
monitoring the established first communication link to determine if the first communication link has been terminated inadvertently; and
automatically re-establishing a new communication link if it is determined that the first communication link was terminated inadvertently.

7. The AED of claim 1, wherein the processor is configured with processor-executable instructions to perform operations further comprising:
automatically transmitting results of periodic self-tests to the remote server via a third communication link to the cellular data network.

8. The AED of claim 1, wherein the processor is configured with processor-executable instructions to perform operations further comprising:
automatically determining whether servicing is needed;
automatically establishing a third communication link to the cellular data network when it is determined that service is needed; and
transmitting a service request to a remote service center server via the established third communication link.

9. The AED of claim 1, further comprising:
a Global Positioning System (GPS) receiver coupled to the processor,
wherein the processor is configured with processor-executable instructions to perform operations further comprising:
receiving location data from the GPS receiver; and
communicating the location data to the remote server via the Internet using the first communication link.

10. A method implemented in an automatic external defibrillator having an integral wireless modem, comprising:
establishing a first communication link with a cellular data network by activating the wireless modem in response to the automatic external defibrillator being activated;
accessing an Internet via the established first communication link;
accessing a remote server via the Internet using the established first communication link;
communicating an activation message to the remote server via the Internet using the established first communication link;
establishing a second communication link with the cellular data network by activating the wireless modem in response to the automatic external defibrillator being deactivated;
accessing the Internet via the established second communication link;
accessing the remote server via the Internet using the established second communication link; and
communicating patient diagnostic data to the remote server via the Internet using the established second communication link.

11. The method of claim 10, further comprising:
placing a cellular telephone call to an emergency services center; and
communicating a verbal message stored in memory identifying a location of the automatic external defibrillator.

12. The method of claim 11, further comprising connecting the cellular telephone call to a speaker phone after the verbal message is communicated to the emergency services center.

13. The method of claim 11,
wherein the remote server is an emergency services center server.

14. The method of claim 10, further comprising:
communicating a location of the automatic external defibrillator to the remote server via the Internet using the established first communication link.

15. The method of claim 10, wherein the remote server is an emergency services center server.

16. The method of claim 10, further comprising:
conducting a voice-over-IP voice call via the established first communication link to the remote server and a speaker phone included within the automatic external defibrillator.

17. The method of claim 10, further comprising:
monitoring the established first communication link to determine if the first communication link has been terminated inadvertently; and
automatically re-establishing a new communication link if it is determined that the established first communication link was terminated inadvertently.

18. The method of claim 10, further comprising:
automatically transmitting results of periodic self-tests to the remote service center server via a third communication link to the cellular data network.

19. The method of claim 10, further comprising:
automatically determining whether servicing of the automatic external defibrillator is needed;
automatically establishing a third communication link with the cellular data network when it is determined that service is needed; and
transmitting a service request to a remote service center server via the established third communication link.

20. The method of claim 10, further comprising:
receiving location data from a Global Positioning System receiver; and
communicating the location data to the remote server via the Internet using the first communication link.

21. An automatic external defibrillator, comprising:
means for establishing a first communication link with a cellular data network in response to the automatic external defibrillator being activated;
means for accessing an Internet via the established first communication link;
means for accessing a remote server via the Internet using the established first communication link;

means for communicating an activation message to the remote server via the Internet using the established first communication link;

means for establishing a second communication link with the cellular data network in response to the automatic external defibrillator being deactivated;

means for accessing the remote server via the Internet using the established second communication link; and communicating patient diagnostic data to the remote server via the Internet using the established second communication link.

22. The automatic external defibrillator of claim 21, further comprising:

means for placing a cellular telephone call to an emergency services center; and means for communicating a verbal message stored in memory identifying a location of the automatic external defibrillator.

23. The automatic external defibrillator of claim 22, further comprising means for connecting the cellular telephone call to a speaker phone after the verbal message is communicated to the emergency services center.

24. The automatic external defibrillator of claim 22, wherein the remote server is an emergency services center server.

25. The automatic external defibrillator of claim 21, further comprising:

means for transmitting a location of the automatic external defibrillator to the remote server via the established first communication link.

26. The automatic external defibrillator of claim 21, wherein the remote server is an emergency services center server.

27. The automatic external defibrillator of claim 21, further comprising:

means for conducting a voice-over-IP voice call via the established first communication link to the remote server and a speaker phone included within the automatic external defibrillator.

28. The automatic external defibrillator of claim 21, further comprising:

means for monitoring the established first communication link to determine if the first communication link has been terminated inadvertently; and means for automatically re-establishing a new communication link if it is determined that the established first communication link was terminated inadvertently.

29. The automatic external defibrillator of claim 21, further comprising:

means for automatically transmitting results of periodic self-tests to a remote service center server via a third communication link to the cellular data network.

30. The automatic external defibrillator of claim 21, further comprising:

means for automatically determining whether servicing of the automatic external defibrillator is needed;

means for automatically establishing a third communication link with the cellular data network when it is determined that service is needed; and means for transmitting a service request to a remote service center server via the established third communication link.

31. The automatic external defibrillator of claim 21, further comprising:

means for receiving location data from a Global Positioning System receiver; and means for transmitting the location data to the remote server.

32. A non-transitory computer-readable medium having stored thereon processor-executable instructions configured to cause a processor within an automatic external defibrillator comprising an integral wireless modem to perform operations, comprising:

establishing a first communication link with a cellular data network in response to the automatic external defibrillator being activated;

accessing an Internet via the established first communication link;

accessing a remote server via the Internet using the established first communication link;

communicating an activation message to the remote server via the Internet using the established first communication link;

establishing a second communication link with the cellular data network in response to the automatic external defibrillator being deactivated;

accessing the Internet via the established second communication link; and communicating patient diagnostic data to the remote server via the Internet using the established second communication link.

33. The non-transitory computer-readable medium of claim 32, wherein the stored processor-executable instructions are configured to cause the processor to perform operations further comprising:

placing a cellular telephone call to an emergency services center; and communicating a verbal message stored in memory identifying a location of the automatic external defibrillator.

34. The non-transitory computer-readable medium of claim 33, wherein the stored processor-executable instructions are configured to cause the processor to perform operations further comprising connecting the cellular telephone call to a speaker phone after the verbal message is communicated to the emergency services center.

35. The non-transitory computer-readable medium of claim 33, wherein the stored processor-executable instructions are configured to cause the processor to perform operations such that the remote server is an emergency services center server.

36. The non-transitory computer-readable medium of claim 32, wherein the stored processor-executable instructions are configured to cause the processor to perform operations further comprising:

transmitting a location of the automatic external defibrillator to the remote server via the established first communication link.

37. The non-transitory computer-readable medium of claim 32, wherein the stored processor-executable instructions are configured to cause the processor to perform operations such that the remote server is an emergency services center server.

38. The non-transitory computer-readable medium of claim 32, wherein the stored processor-executable instructions are configured to cause the processor to perform operations further comprising:

conducting a voice-over-IP voice call via the established first communication link to the remote server and a speaker phone included within the automatic external defibrillator.

39. The non-transitory computer-readable medium of claim 32, wherein the stored processor-executable instructions are configured to cause the processor to perform operations further comprising:

monitoring the established first communication link to determine if the first communication link has been terminated inadvertently; and automatically re-establishing a new data communication link if it is determined that the established first communication link was terminated inadvertently.

40. The non-transitory computer-readable medium of claim 32, wherein the stored processor-executable instructions are configured to cause the processor to perform operations further comprising:

automatically transmitting results of periodic self-tests to a remote service center server via a third communication link to the cellular data network.

41. The non-transitory computer-readable medium of claim 32, wherein the stored processor-executable instructions are configured to cause the processor to perform operations further comprising:

automatically determining whether servicing of the automatic external defibrillator is needed;

automatically establishing a third communication link with the cellular data network when it is determined that service is needed; and transmitting a service request to a remote service center server via the established third communication link.

42. The non-transitory computer-readable medium of claim 32, wherein the stored processor-executable instructions are configured to cause the processor to perform operations further comprising:

receiving location data from a Global Positioning System receiver; and transmitting the location data to the remote server.

* * * * *